United States Patent [19]

Yapel, Jr.

[11] 4,169,804
[45] Oct. 2, 1979

[54] MAGNETICALLY RESPONSIVE COMPOSITE MICROPARTICLE

[75] Inventor: Anthony F. Yapel, Jr., Roseville, Minn.

[73] Assignee: Minnesota Mining and Manufacturing Company, St. Paul, Minn.

[21] Appl. No.: 808,334

[22] Filed: Jun. 20, 1977

Related U.S. Application Data

[63] Continuation-in-part of Ser. No. 715,901, Aug. 19, 1976, abandoned.

[51] Int. Cl.² ............ A61K 9/50; A61K 9/38; G01N 33/16
[52] U.S. Cl. ............ 252/62.53; 252/62.54; 424/36
[58] Field of Search ............ 424/1, 36; 252/62.53, 252/62.54

[56] References Cited

U.S. PATENT DOCUMENTS

| | | | |
|---|---|---|---|
| 650,760 | 5/1900 | Metcalf | 424/37 |
| 2,971,916 | 2/1961 | Schleicher et al. | 252/62.53 |
| 3,041,289 | 6/1962 | Katchen et al. | 252/316 |
| 3,042,616 | 7/1962 | Brown | 252/62.53 |
| 3,137,631 | 7/1964 | Soloway | 424/36 |
| 3,522,346 | 7/1970 | Chang | 424/35 |
| 3,725,113 | 4/1973 | Chang | 424/36 X |
| 3,933,997 | 1/1976 | Hersh et al. | 424/1 |
| 3,937,668 | 2/1976 | Zolle | 252/316 |
| 3,980,764 | 9/1976 | Adams | 424/1 |

OTHER PUBLICATIONS

Kramer; J. Pharmaceutical Sciences, vol. 63, No. 10, pp. 1646, 1647, 10/74.

*Primary Examiner*—F. C. Edmundson
*Attorney, Agent, or Firm*—Cruzan Alexander; Donald M. Sell; James V. Lilly

[57] ABSTRACT

Magnetically responsive composite microparticles comprising (i) a magnetically responsive material and (ii) a porous solid water-insoluble matrix selected from proteinaceous materials, polysaccharides and mixtures thereof; wherein said magnetically responsive material is dispersed throughout said permeable, solid, water-insoluble matrix.

18 Claims, 2 Drawing Figures

MAGNETICALLY RESPONSIVE COMPOSITE MICROPARTICLE

CROSS REFERENCE TO RELATED APPLICATION

This application is a Continuation-In-Part of copending application Ser. No. 715,901, filed Aug. 19, 1976, now abandoned.

BACKGROUND OF THE INVENTION

This invention relates to magnetically responsive composite materials. More particularly it relates to magnetically responsive composite microparticles having a permeable, solid, water-insoluble matrix comprising a proteinaceous material, a polysaccharide or mixtures thereof.

Water-insoluble proteinaceous or polysaccharide microparticles are known. For example, U.S. Pat. No. 3,663,685 describes physiologically acceptable parenterally metabolizable protein or polysaccharide microparticles. U.S. Pat. Nos. 3,663,686 and 3,663,687 each describe physiologically acceptable, parenterally metabolizable protein microparticles while U.S. Pat. No. 3,758,678 describes physiologically acceptable, parenterally metabolizable polysaccharide microparticles. These microparticles are, or can be made, radioactive and can be employed for diagnostic, prophylactic or therapeutic purposes.

Water-insoluble protein or polysaccharide microparticles have also found use in labeling medicaments so that the source of the medicament can later be identified. They have also been used as carriers for various drugs.

Such microparticles have been well accepted. The present invention, however, provides an improvement thereover.

SUMMARY OF THE INVENTION

In accordance with the present invention there is provided a magnetically responsive composite microparticle comprising (i) a magnetically responsive material and (ii) a permeable, solid water-insoluble matrix selected from proteinaceous materials, polysaccharides and mixtures thereof; wherein said magnetically responsive material is dispersed throughout said water-insoluble matrix.

In another aspect of the invention there is also dispersed throughout the matrix a combining agent which is capable of sorbing substances present in biological fluids.

As it is used herein, the term "sorb" means "to collect one material either (i) on the surface of, or (ii) within the body of a second material". Thus the term "sorb" includes adsorb and absorb; the term "sorbent" includes adsorbent and absorbent; the term "sorption" includes adsorption and absorption.

Microparticles of the present invention are useful in a variety of applications. For example, they may be substituted for prior art microparticles in labeling or carrying medicaments and drugs. Because of their magnetic responsiveness, they are easily retrieved or relocated without the need to employ expensive equipment.

Microparticles of the present invention are also useful in chemical reactions. For example, microparticles having a water-insoluble enzyme matrix can be utilized to catalyze certain chemical reactions and can then be easily recovered from the reaction mixture by applying a magnetic field thereto.

Microparticles of the present invention are also useful in in vitro techniques for determining concentrations of substances present in biological fluids (e.g., serum and urine). Commonly these techniques involve competitive binding of the substance whose concentration is to be determined, and a radioactively labeled analog thereof, to binding sites on a specific receptor (usually a protein or antibody). The portion of the substance bound to the receptor is then separated from that portion not bound to the receptor and counted for radioactivity. The concentration of the substance is then determined by comparing the counted radioactivity with a standard curve.

A variety of materials and techniques have been employed to separate the bound and unbound fractions. They include, for example, differential migration of the bound and free fractions (e.g., by electrophoresis, chromatoelectrophoresis, gel filtration, etc.); chemical precipitation of the bound or free fraction (e.g., by means of organic solvents, salts, acids, etc.); immunological precipitation of the bound fraction (e.g., by the double antibody method); adsorption of the bound or free fraction onto selective sorbing media (e.g., charcoal, silicates, resins, etc.).

Some of these techniques require rather complicated procedures in order to bring about separation of the bound and free fractions. Such procedures reduce operator efficiency and increase the cost of the tests. As a result, they are not suited to large scale operations. Other of these techniques do not adequately distinguish between the bound and free fractions and, therefore, lack the accuracy preferred in in vitro testing. Still other of these techniques can only be utilized in a limited number of tests.

Recently attempts have been made to simplify in vitro testing for materials present in biological fluids. For example, U.S. Pat. No. 3,933,997 discloses a process and composition useful in determining concentrations of digoxin in body fluids. The composition consists of anti-digoxin antibodies covalently bonded to an intermediate silane which is in turn coupled to magnetically responsive particles. The particles can be magnetically separated from the test solution.

Antibodies used in such a composition are, therefore, coupled to the surface of the particles thereby limiting the amount of antibody present thereon. When such compositions are prepared from anti-sera having low titer, certain particles may not have any antibody bonded thereto. Additionally, the process of covalently bonding the antibody to the intermediate silane must be carefully controlled so that the complexing ability of the antibody is not lost. Moreover, this composition is useful only in determining concentrations of digoxin.

U.S. Pat. No. 3,970,518 discloses small magnetic particles whose surface is coated with a layer of antibody. Such coated magnetic particles are useful in sorting out and separating select viruses, bacteria and other cells from multicell, bacteria or virus populations. The amount of antibody in such compositions available for sorting and separating is also limited by the available external surface area of the magnetic material.

Composite microparticles of the present invention overcome these deficiencies of the prior art. They provide compositions wherein the permeable, solid matrix of the microparticle itself is capable of sorbing substances present in biological fluids (e.g., drugs, hormones, vitamins, proteins, enzymes). Additionally, the sorptive properties of the microparticles of the invention are not lost during their preparation. Still further the microparticles of the invention have a substantially greater binding capacity than do prior art compositions. This is because the present microparticles are permeable thereby allowing biological fluids to penetrate into the interior of the particle and be sorbed therein. As a result the binding capacity of the present invention is not limited by the amount of external surface area of the particle. Moreover, microparticles of the invention may be used in a variety of in vitro diagnostic tests.

Composite microparticles of the invention are useful in determining the concentration of a variety of substances in biological fluids in a rapid, efficient and accurate manner. Thus they may be employed to measure the amount of such substances as drugs (e.g., digoxin and antibiotics), hormones (e.g., thyroxine), vitamins (e.g., vitamin $B_{12}$), proteins, enzymes, etc. Because of their magnetic responsiveness they are rapidly and efficiently separable from the test solution. Moreover, they are simple to use and eliminate the necessity to employ complicated and expensive separation techniques. Thus they are particularly useful in large scale testing wherein a number of separate samples were tested at the same time. Moreover the microparticles of the invention may be designed to sorb a specific substance or a variety of substances.

BRIEF DESCRIPTION OF THE DRAWINGS

The present invention is described in more detail hereinafter with reference to the accompanying drawings in which the same reference numbers refer to the same elements throughout the several views and in which.

DETAILED DESCRIPTION OF THE INVENTION

Figure 1:
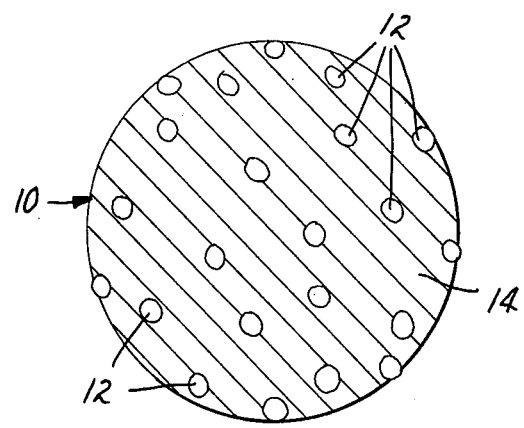
FIG. 1 is a cross-sectional view of one embodiment of the invention.

Referring now specifically to FIG. 1 there is shown a cross-sectional view of a composite microparticle 10 of the invention comprising a magnetically responsive material 12 dispersed throughout a permeable, solid, water-insoluble proteinaceous matrix 14. The magnetically responsive material 12 is typically uniformly dispersed throughout the microparticle. Additionally, some of the magnetically responsive material projects from the exterior surface of the microparticle so as to be partially exposed as shown in the Figures.

Figure 2:
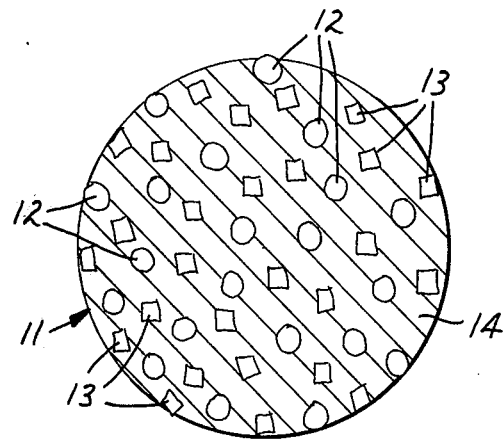
FIG. 2 is a cross-sectional view of an alternative embodiment of the invention.

FIG. 2 shows a cross-sectional view of a composite microparticle 11 of the invention comprising a magnetically responsive material 12 and a combining agent 13 each of which is dispersed throughout a permeable, solid, water-insoluble proteinaceous matrix 14. The combining agent 13 is typically uniformly dispersed throughout the microparticle. Additionally some of the combining agent projects from the exterior surface of the microparticle so as to be partially exposed.

The indicia employed to represent magnetically responsive material 12 and combining agent 13 are intended for illustrative purposes only and are not meant to limit the invention. Moreover, the shape of magnetically responsive material 12 and combining agent 13 is not critical to the invention.

Composite microparticles of the present invention may be conveniently prepared. Usually the particles are spherical although it is not necessary that they be so. In any event, their surfaces may be either substantially smooth (e.g., having no major irregularities therein) or rough (e.g., having numerous cavities therein). The size of the particles is not critical to the present invention, it being understood that, for a given mass of microparticles, the surface area increases as the diameter of the particles decreases. In any event, the maximum dimension of the particles may vary over a wide range. Typically their maximum dimension is in the range of about 5 to 400 microns. Preferably it is in the range of about 10 to 250 microns.

Suitable magnetically responsive materials for use in microparticles of the present invention are water-insoluble. Additionally, it is preferred they have a high magnetic permeability so that the field of the magnet used to separate the composites in the process described hereinafter will be "focused" therein thereby allowing rapid and thorough retrieval of the particles.

The quantity of magnetically responsive material present in the microparticles may vary. Preferably it comprises from about 5 to 75% by weight of the microparticles. Most preferably it comprises from about 45 to 75% by weight of the microparticles.

Representative examples of useful magnetically responsive materials include ferromagnetic substances such as the metallic oxides (e.g., $BaFe_{12}O_{19}$, $Fe_3O_4$, $CoO$, $NiO$, $Mn_2O_3$) iron and nickel particles, etc. Another useful ferromagnetic material is CoMnP.

Matrices suitable for use in the present invention may be prepared from proteinaceous materials, polysaccharides and mixtures thereof. The proteinaceous materials may be either naturally occurring (e.g., albumins) or synthetic (e.g., synthetic polypeptides). In either event they are polymers which are primarily comprised of carbon, hydrogen, oxygen, sulfur and nitrogen and which have the general formula

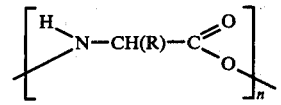

Their molecular weights may range from a few thousand to several hundred thousand. They may be used singly or in combination in preparing the matrix.

Representative examples of useful natural proteinaceous materials include albumin, gelatin, globulins (e.g., antibodies) and enzymes. Representative examples of useful polypeptides include polylysine and polyglutamic acid.

Representative examples of useful polysaccharides include starch, acacia, gum ghatti, gum xanthan, gum karaya, gum tragacanth, carragheenan, pectin, and polygalacturonic acid, glycogen or dextran.

When used in determining the concentration of a given substance in a biological fluid, the matrix of the microparticles may itself sorb the substance or, alternatively, it may contain a combining agent which sorbs the substance. In either event the sorption may be general, that is the matrix or combining agent may be capable of sorbing a number of substances, or it may be specific, that is the matrix or combining agent may be capable of sorbing only a particular substance.

Combining agents useful in the present invention are those materials which join with substances present in biological fluids. The exact mechanism by which these agents join with such substances is not completely understood. However, it is believed that some of such agents react with oppositely charged groups on the substance whose concentration is being determined, while others are believed to form covalent bonds with the substance. It is also believed that still others form bonds with the substance through van der Waals forces, hydrophobic bonds, etc.

In any event the combining agents useful in the present invention include general sorbents for the substance (e.g., granulated charcoal and ion-exchange resins) and specific sorbents for the substance (e.g., thyroxine antibody for T-4 or fish serum such as sockeye salmon serum, oyster toadfish serum and rainbow trout serum or intrinsic factor for vitamin $B_{12}$). Non-proteinaceous specific sorbents may also be used. Granulated charcoal is useful in the present invention when the concentration of vitamin $B_{12}$ is being determined. Ion-exchange resins of the anionic variety, are useful when the concentration of thyroxine (T-4) is to be determined.

Ion-exchange resins may be broadly categorized as insoluble acids or bases which remain insoluble when converted to salts. They contain fixed electronegative or electropositive charges. Thus cation-exchange resins are those which contain fixed electronegative charges while anion-exchange resins are those which contain fixed electropositive charges.

Ion-exchange resins may be organic or inorganic solids or liquids. Preferably they are organic polymers. They may be classified as strong-acid and weak-base materials. Each of the ion-exchange resins have active groups associated therewith. Representative examples of these active groups are sulfonic, carboxylic and phosphonic acid groups, quaternary ammonium groups; and secondary and tertiary amine groups.

Commonly used polymeric ion-exchange resins are based upon crosslinked polystyrene (e.g., sulfonated copolymers of styrene and divinylbenzene). Quaternary ammonium derivatives of this copolymer provide strong-base anion-exchange resins while secondary and tertiary amine derivatives provide weak-base anion-exchange resins.

Other useful ion-exchange resins include copolymers of (i) acrylic and methacrylic acids or esters or the corresponding nitriles and (ii) the condensation product of epichlorohydrin with amines.

The above-described ion-exchange resins are further discussed in *Encyclopedia of Polymer Science and Technology*, Vol. 7, Interscience Publishers 1967, pages 692–723 incorporated herein by reference.

Representative examples of commercially available ion-exchange resins of the type described above include "Dowex 1" and "Dowex 2" (crosslinked polystyrene-quaternary ammonium resin available from Dow Chemical Co.); "Amberlite 400" (crosslinked polystyrene-quaternary ammonium resin available from Rohm and Haas Company). Other examples of useful commercially available ion-exchange resins may be found in the *Encyclopedia of Polymer Science and Technology*, Vol. 7, Interscience Publishers 1967, at pages 696–698.

Still other useful ion-exchange resins include those disclosed in U.S. Pat. No. 3,702,821. These resins comprise crosslinked polystyrene-quaternary ammonium resin treated with a chelating agent. Useful chelating agents include hydroxy and carboxylic acids, inorganic anions which have sequestering properties such as fluoride and phosphate, etc.

The amount of combining agent employed in the matrix is not critical to the present invention provided that there is sufficient agent present to join with the substance whose concentration is being measured. Thus the amount is primarily dependent upon the agent used and the substance whose concentration is to be determined.

As stated above, the magnetically responsive composite microparticles may be conveniently prepared. For example, composite particles which employ no combining agent may be made by mixing the magnetically responsive material with an aqueous solution of a matrix-forming material and injecting the mixture through a hypodermic needle into a heated and vigorously stirred bath liquid with which the mixture is incompatible, such as a bath of vegetable oil, to form microparticles which are crosslinked by the heat and thereby made water-insoluble. The resulting particles may then be collected and purified by filtering the bath and washing the filtrate with organic solvents (e.g., heptane) and water. Other ingredients such as diluents may also be included in the mixture prior to its injection into the bath.

Alternatively, they may be made by injecting the mixture of magnetically responsive material and matrix-forming material into a vigorously stirred bath liquid of an incompatible material such as vegetable oil, heating the resultant dispersion to drive off water, collecting the microparticles (e.g., by filtration) and heating the microparticles until they become insolubilized.

In an alternative process the composites may be prepared by a room temperature technique by injecting a mixture of magnetically responsive material and aqueous solution of proteinaceous material into a stirred bath of vegetable oil containing a lipophilic drying agent and a crosslinking agent. This technique is also useful in preparing composite microparticles which employ a combining agent. The agent should be added to the mixture before injection into the vegetable oil. The dispersion is preferably maintained for about two hours during which time the dispersed droplets are dehydrated and proteinaceous material in the dispersed phase is crosslinked. The resultant water-insoluble composite microparticles may then be collected and purified as described above.

Suitable lipophilic drying agents include aliphatic alcohols such as n-butanol, 2-ethylhexanol, etc. The amount of drying agent employed is not critical to the invention provided that a sufficient amount is used so as to dissolve substantially all of the water present in the reaction solution.

Suitable crosslinking agents include aldehydes such as formaldehyde and glutaric dialdehyde. Although the amount of crosslinking agent employed may vary, it is preferred that it comprise from about 2 to 5 parts by weight of the proteinaceous material to be crosslinked.

Despite being crosslinked and rendered water-insoluble during preparation of the microparticles, the proteinaceous or polysaccharide material, whether present as matrix material or combining agent, retains sufficient activity to sorb substances in biological fluids. Moreover, the microparticles retain their permeability despite being crosslinked. Thus the particles increase in size (e.g., swell) as biological fluids penetrate them.

The particle size range of the microspheres can be controlled by varying either or both the rate of injection and the degree of agitation. Moreover, the addition of small amounts of surfactants (e.g., 0.1–2% by weight of the injected solution) also influences the size of the microspheres.

Once prepared the microparticles are preferably formed into tablets by techniques known to the art. An excipient, or combination thereof, is employed to maintain the integrity of the tablet. Excipients employed should not affect either the sorptive properties of the matrix or the results of the assay. Additionally it is preferred that they permit the tablet to rapidly dissolve and disperse in test solutions. Once prepared the tablets are exposed to a strong magnetic field for about one second so as to magnetize them. However, once dispersed the microparticles do not substantially reagglomerate until subjected to an external magnetic field.

The magnetized tablets are especially convenient to use because they contain a predetermined amount of the microparticles. Thus, the need to weigh the microparticles prior to addition to the test solution is eliminated.

Tablets comprising about 10 to 30% by weight composite microparticles and, correspondingly, 90 to 70% by weight excipient are preferred. However, other ratios of ingredients may also be employed.

Excipients which are useful in the tablet include lactose (U.S.P.), pregelatinized starch (U.S.P.), corn starch (U.S.P.), unmilled dicalcium phosphate (N.F.), microcrystalline cellulose (N.F.), etc.

As stated above, the composite particles of the invention can be employed to determine the concentration of substances present in physiological fluids. While the determination may be carried out by a variety of techniques, one of the following two procedures is commonly used. In the first, predetermined amounts of the following ingredients are employed:

(a) a biological fluid containing the substance whose concentration is to be measured;
(b) a radioactively labeled form of that substance; and
(c) composite microparticles of the invention wherein a combining agent which specifically sorbs the substance is included within the matrix or wherein the matrix itself specifically sorbs the substance. The ingredients are reacted so as to cause the substance whose concentration is to be determined and its labeled form to competitively complex with the available sites on the microparticles. The resultant complexed microparticles are then magnetically separated from the reaction solution and the radioactivity of either the composite microparticles or the remaining reaction solution counted. The concentration of the substance to be measured is then determined by comparing the counted radioactivity with a standard curve.

The exact amounts of the labeled form of the substance and the magnetically responsive microparticles used in this process are selected so that there is an excess of the labeled substance over the total number of sites available for complexing on the microparticles. This insures that the labeled and unlabeled forms of the substance will compete for the sites.

In the second process, predetermined amounts of the following ingredients are employed:

(a) a biological fluid containing the substance whose concentration is to be measured;
(b) a radioactively labeled form of that substance;
(c) a specific binding agent for the substance; and
(d) composite microparticles of the invention containing a combining agent in the matrix which is a general sorbent, or where the matrix itself acts as a general sorbent. Ingredients (a), (b) and (c) are reacted to cause the substance and its labeled form to competitively bind to the available binding agent. The microparticles (d) are then added to, and reacted with, the mixture so as to cause that portion of both the substance and its labeled form not bound to the binding agent (that is, the free forms thereof) to complex with the available sites on the microparticles. The resultant complexed microparticles are then magnetically separated and the concentration of the substance determined as described above.

In this method the amount of specific binding agent should be selected so that neither all of the substance or its labeled form becomes bound thereto. The quantity of microparticles employed should be selected so that substantially all of the free portions of the substance and its labeled form complex therewith. Thus the quantity of microparticles should provide more sites for complexing than there is free substance and free labeled substance.

The reactions employed in these methods are generally carried out at room temperature (e.g., 20°–25° C.) in a short time (e.g., 10–30 minutes). Preferably, the reactions are carried out with agitation.

Frequently, the substance whose concentration is to be determined is attached to or combined with other materials in the test sample. Such attached or combined substances, also referred to as endogenous substances, are preferably liberated from these materials so as to improve the accuracy of the assay. Various techniques for liberation may be employed and are well known to those in the art. Thus, for example, thermal or chemical techniques may be employed.

Various techniques may be employed in order to separate the microparticles of the invention from the test sample. For example, they may be separated by placing a permanent magnet in close proximity to the vessel containing the test sample and then decanting the liquid portion thereof. Alternatively, an electromagnet may be employed in place of the permanent magnet. Devices for quickly, easily and automatically causing the separation of the magnetic microparticles from the sample may be employed.

The following examples are meant to further illustrate without limiting the present invention.

EXAMPLE 1

Magnetically responsive composite microparticles having magnetically responsive material dispersed throughout a permeable, solid, crosslinked, water-insoluble protein matrix were prepared in the following way. To 2.0 ml of deionized water were added 0.06 gram (g) of a magnetically responsive material (ferrosoferric oxide, $Fe_3O_4$) and 1.00 g of human serum albumin (HSA). The mixture was stirred until all the HSA was dissolved and the $Fe_3O_4$ particles well suspended. Using a 5 ml syringe equipped with a 20 gauge hypodermic needle, this aqueous mixture was then injected into a rapidly stirred (1200 rpm) continuous phase consisting of 170 ml. cottonseed oil at room temperature (22° C.) to produce a dispersion of the aqueous mixture in the continuous phase. The dispersion was heated with continuous stirring at 130° C. over a 20 minute time interval and held at this temperature for one hour to dewater and crosslink the protein matrix. The resulting solid microparticles were collected by pressure filtration (using an Amicon Model 402 ultrafiltration cell) on a 0.22 micron pore size Millipore filter. Residual oil was removed by washing the microparticles with three 300 ml. aliquots of heptane. The microparticles were then dried by passing a stream of dry nitrogen gas over them for one-half hour. The dried microparticles were spherical and had diameters in the range of about 10 to 100 microns. These microparticles are useful in sorbing T-4 in human serum.

EXAMPLE 2

Magnetically responsive composite microparticles having magnetically responsive material dispersed throughout a permeable, solid, crosslinked, water-insoluble protein matrix were prepared by dissolving 1.00 gram of HSA to which was added 0.064 g of the magnetically responsive material CoMnP in 2.0 ml of deionized water. The ferromagnetic material was uniformly dispersed through the protein solution with the aid of a tissue grinder. This aqueous mixture was then injected through a 20 gauge needle into 500 ml of a rapidly stirred (1300 rpm) continuous phase consisting of 500 ml of cottonseed oil to produce a dispersion of the aqueous mixture in the continuous phase. The dispersion was heated with continued stirring to 140° C. over a one and one-half hour period and held at this temperature for an additional hour to dewater and crosslink the protein matrix. The resulting microparticles were collected by vacuum filtration, washed with three 100 ml aliquots of heptane, and then air dried at room temperature. The dried microparticles were spherical and had diameters in the range of about 10 to 100 microns. These microparticles are useful in sorbing T-4 in human serum.

EXAMPLE 3

Magnetically responsive composite microparticles having magnetically responsive material dispersed throughout a permeable, solid, crosslinked, water-insoluble protein matrix were prepared. An aqueous mixture comprising 0.1 gram (g) of magnetically responsive material (barium ferrite $BaFe_{12}O_{19}$) in 1.5 milliliter (ml) of protein solution (bovine serum albumin in water, 0.35 g/ml) was added dropwise into a rapidly stirred, continuous phase comprising 200 ml dewatering agent (n-butanol), 2.4 ml crosslinking agent (formaldehyde, 35% by weight in water) and 200 ml oil (castor oil) to produce a dispersion of the aqueous mixture in the continuous phase. The dispersion was mixed for two hours at room temperature (e.g., 22° C.) to crosslink the protein matrix. The resulting solid microparticles were collected by vacuum filtration. Residual oil was removed by contacting the microparticles with n-heptane in a Soxhlet extractor for about 18 hours. Residual water-soluble components were then removed in a similar manner by contacting the microparticles with water in the Soxhlet extractor for about ten hours. The microparticles were then vacuum dried at 80° C. for 24 hours. The dried microparticles were spherical and had diameters in the range of about 10 to 100 microns. These microparticles were useful in sorbing T-4 in human serum.

EXAMPLE 4

Magnetically responsive composite particles having magnetically responsive material dispersed throughout a heat-denatured, permeable, solid, water-insoluble protein matrix were prepared. An aqueous mixture comprising 0.5 g of magnetically responsive material ($BaFe_{12}O_{19}$) in 1.5 ml of protein (bovine serum albumin in water, 0.35 g/ml) was added dropwise to 3 liters of rapidly stirred cottonseed oil to produce a dispersion of the mixture in the oil. The dispersion was heated for 3 hours at about 120° to 130° C. to denature and dehydrate the protein matrix and provide water-insoluble particles. The particles were collected by vacuum filtration. Residual oil was removed from the particles by contacting the particles with n-heptane in a Soxhlet extractor for about 20 hours. Residual water-soluble components were then removed from the particles in a similar manner by contacting the particles with water in a Soxhlet extractor. The resulting particles were vacuum dried at 80° C. for 24 hours. The dried particles were spherical and had diameters in the range of about 10 to 250 microns. These microparticles were useful in sorbing T-4 in human serum.

EXAMPLE 5

Magnetically responsive composite particles having magnetically responsive material and a non-proteinaceous sorbent dispersed throughout a porous, solid, crosslinked, water-insoluble protein matrix were prepared according to the procedures described in Example 3. The aqueous mixture comprised 1.3 g of magnetically responsive material ($BaFe_{12}O_{19}$), 2.6 g of non-proteinaceous sorbent (granulated charcoal) and 1.5 ml of protein solution (bovine serum albumin in water, 0.35 gm/ml). The continuous phase comprised 500 ml dewatering agent (n-butanol), 20 ml crosslinking agent (formaldehyde, 35% by weight in water), and 500 ml of oil (castor oil). The resulting magnetically responsive particles were spherical and had diameters in the range of from about 40 to 400 microns. These microparticles were useful in sorbing vitamin $B_{12}$ in human serum.

EXAMPLE 6

Magnetically responsive composite particles were prepared as described in Example 3. An aqueous mixture (5 ml) comprising 1.5 g of magnetically responsive material ($BaFe_{12}O_{19}$), 2 ml of sockeye salmon serum and bovine serum albumin (0.35 g/ml) was added dropwise into a rapidly stirred continuous phase comprising 500 ml of dewatering agent (n-butanol), 20 ml of crosslinking agent (formaldehyde, 35% by weight in water) and 500 ml of oil (castor oil). The resultant particles were spherical and had diameters in the range of about 10 to 100 microns. They were useful in sorbing vitamin $B_{12}$ in human serum.

EXAMPLE 7

Magnetically responsive composite microparticles having magnetically responsive material dispersed throughout a permeable, solid crosslinked, water-insoluble polysaccharide matrix were prepared in the following way. To 4.0 ml of deionized water was added 1.00 gm of the polysaccharide acacia (Fisher Scientific) with stirring. After the acacia had dissolved completely, 0.20 gm of the magnetically responsive material ferrosoferric oxide, $Fe_3O_4$ was added with continued stirring until the $Fe_3O_4$ particles were well suspended. Using a 5 ml syringe equipped with a 22 gauge hypodermic needle, this aqueous mixture was then injected into a rapidly stirred (2000 rpm) continuous phase consisting of 500 ml of cottonseed oil at room temperature (23° C.) to produce a dispersion of the aqueous mixture in the continuous phase. The dispersion was heated with continuous stirring to 170° C. over a 25 minute time period and held at this temperature for an additional two hours to dewater and crosslink the polysaccharide matrix. The resulting solid, water-insoluble microparticles were collected by vacuum filtration, washed with three 100 ml aliquots of heptane, and then air dried at room temperature. The dried microparticles were spherical and had diameters in the range of about 10 to 50 microns. They were useful in sorbing T-4 in human serum.

What is claimed is:

1. A magnetically responsive composite microparticle consisting essentially of (i) a magnetically responsive material, and (ii) a water permeable, solid, water-insoluble matrix selected from the group consisting of proteinaceous materials, polysaccharides and mixtures thereof; wherein said magnetically responsive material is dispersed throughout said water-insoluble matrix.

2. A composite microparticle according to claim 1 wherein said water permeable, solid, water-insoluble matrix is derived from a proteinaceous material.

3. A composite microparticle according to claim 2 wherein said proteinaceous material is selected from the group consisting of albumins, gelatin, globulins and enzymes.

4. A composite microparticle according to claim 3 wherein said proteinaceous material is an albumin.

5. A composite microparticle according to claim 3 wherein said proteinaceous material is a globulin.

6. A composite microparticle according to claim 3 wherein said proteinaceous material is an enzyme.

7. A composite microparticle according to claim 3 wherein said proteinaceous material is gelatin.

8. A composite microparticle according to claim 1 wherein said water-permeable, water-insoluble matrix is derived from a polysaccharide.

9. A composite microparticle according to claim 1 wherein said magnetically responsive material is a ferromagnetic material.

10. A composite microparticle according to claim 9 wherein said ferromagnetic material is selected from the group consisting of $BaFe_{12}O_{19}$, $Fe_3O_4$, $CoO$, $NiO$, $Mn_2O_3$, $CoMnP$, iron particles and nickel particles.

11. A composite microparticle according to claim 1 wherein said water-permeable microparticle has a maximum dimension in the range of about 5 to 400 microns.

12. A composite microparticle according to claim 1 wherein there is further included in said water-insoluble matrix a combining agent capable of sorbing substances present in biological fluids, wherein said combining agent is selected from the group consisting of activated charcoal, ion-exchange resins, and binding proteins which have a specific affinity for said substances.

13. A composite microparticle according to claim 12 wherein said combining agent is charcoal.

14. A composite microparticle according to claim 12 wherein said combining agent is an ion-exchange resin.

15. A composite microparticle according to claim 14 wherein said ion-exchange resin contains fixed electronegative charges.

16. A composite microparticle according to claim 14 wherein said ion-exchange resin contains fixed electropositive charges.

17. A composite microparticle according to claim 12 wherein said combining agent is a binding protein which has a specific affinity for said substances.

18. A composite microparticle according to claim 17 wherein said binding protein is selected from the group consisting of thyroxine antibody, intrinsic factor and fish serum.

* * * * *

UNITED STATES PATENT AND TRADEMARK OFFICE
CERTIFICATE OF CORRECTION

PATENT NO. : 4,169,804
DATED : October 2, 1979
INVENTOR(S) : Anthony F. Yapel, Jr.

It is certified that error appears in the above-identified patent and that said Letters Patent are hereby corrected as shown below:

Col. 12, line 9, change "said water-permeable microparticle"
to --said microparticle--.

Col. 12, line 12, change "said water-insoluble" to
--said water-permeable water-insoluble--.

Signed and Sealed this

Twenty-ninth Day of January 1980

[SEAL]

Attest:

SIDNEY A. DIAMOND

Attesting Officer

Commissioner of Patents and Trademarks